United States Patent
Taguchi et al.

(10) Patent No.: US 9,651,506 B2
(45) Date of Patent: May 16, 2017

(54) SPECTRAL RESPONSE EFFECTS (SRE) COMPENSATION METHOD FOR PHOTON COUNTING DETECTORS (PCDS)

(71) Applicant: THE JOHNS HOPKINS UNIVERSITY, Baltimore, MD (US)

(72) Inventors: Katsuyuki Taguchi, Elkridge, MD (US); Somesh Srivastava, Waukesha, WI (US)

(73) Assignee: The Johns Hopkins University, Baltimore, MD (US)

( * ) Notice: Subject to any disclaimer, the term of this patent is extended or adjusted under 35 U.S.C. 154(b) by 104 days.

(21) Appl. No.: 14/764,707

(22) PCT Filed: Jan. 31, 2014

(86) PCT No.: PCT/US2014/014150
§ 371 (c)(1),
(2) Date: Jul. 30, 2015

(87) PCT Pub. No.: WO2014/121072
PCT Pub. Date: Aug. 7, 2014

(65) Prior Publication Data
US 2015/0355114 A1 Dec. 10, 2015

Related U.S. Application Data

(60) Provisional application No. 61/759,072, filed on Jan. 31, 2013.

(51) Int. Cl.
*G01N 23/04* (2006.01)
*G01N 23/087* (2006.01)
(Continued)

(52) U.S. Cl.
CPC ......... *G01N 23/087* (2013.01); *A61B 6/4241* (2013.01); *A61B 6/481* (2013.01); *A61B 6/482* (2013.01); *A61B 6/5205* (2013.01); *A61B 6/5217* (2013.01); *A61B 6/585* (2013.01); *A61B 6/586* (2013.01); *G01N 23/04* (2013.01);
(Continued)

(58) Field of Classification Search
CPC ....... A61B 6/032; A61B 6/4241; A61B 6/482; G01N 23/04; G01N 2223/423
See application file for complete search history.

(56) References Cited

U.S. PATENT DOCUMENTS

2002/0179844 A1  12/2002 Lundqvist
2004/0017224 A1  1/2004 Tumer
(Continued)

FOREIGN PATENT DOCUMENTS

WO  2010-062291 A1  6/2010

*Primary Examiner* — Hoon Song
(74) *Attorney, Agent, or Firm* — Johns Hopkins Technology Ventures

(57) ABSTRACT

An embodiment in accordance with the present invention provides a new SR compensation (SRC) method, using a more efficient conjugate gradient method. In this method, the first and second derivatives are directly calculated analytically. The proposed SRC uses a sinogram restoration approach, integrates the SRF as a part of a forward imaging model, and compensates for the effect of the SR by maximizing the Poisson log-likelihood of measurements. The algorithm can be evaluated using as a simulated fan-beam x-ray CT scanner.

20 Claims, 7 Drawing Sheets

(51) Int. Cl.
 *A61B 6/03* (2006.01)
 *A61B 6/00* (2006.01)
(52) U.S. Cl.
 CPC ............ *A61B 6/032* (2013.01); *A61B 6/4035* (2013.01); *A61B 6/4078* (2013.01); *A61B 6/483* (2013.01); *A61B 6/5294* (2013.01)

(56) References Cited

U.S. PATENT DOCUMENTS

| | | |
|---|---|---|
| 2008/0099689 A1 | 5/2008 | Nygard et al. |
| 2008/0135789 A1* | 6/2008 | Du .................... A61B 6/032 250/580 |
| 2009/0310744 A1* | 12/2009 | Petch .................. A61B 6/4241 378/53 |
| 2011/0101231 A1 | 5/2011 | Rundle |
| 2013/0108013 A1* | 5/2013 | Leng .................... A61B 6/032 378/19 |

* cited by examiner

```
* COMPUTE INITIAL GUESS OF l
* DO
  * COMPUTE GRADIENT, g = ∇Φ, USING THE CHAIN RULE
  * COMPUTE SEARCH DIRECTION, d, USING THE CONJUGATE GRADIENT METHOD
  *DO
    * UPDATE l USING QUASI-NEWTON METHOD APPLIED ALONG d
  *WHILE (WOLFE CONDITIONS (NOCEDAL AND WRIGHT[4], PAGE 33) ARE NOT SATISFIED)
*WHILE (GRADIENT, g, IS LARGE
```

FIG. 2

DENSITY DISTRIBUTION OF WATER BASIS MATERIAL (g/cc)

CONCENTRATION DISTRIBUTION OF I BASIS MATERIAL (mol/L)

CONCENTRATION DISTRIBUTION OF Gd BASIS MATERIAL (mol/L)

SPECTRAL RESPONSE EFFECTS (SRE) COMPENSATION METHOD FOR PHOTON COUNTING DETECTORS (PCDS)

CROSS-REFERENCE TO RELATED APPLICATIONS

This application is a 35 U.S.C. §371 U.S. national entry of International Application PCT/US2014/014150, having an international filing date of Jan. 31, 2014, which claims the benefit of U.S. Provisional Application No. 61/759,072, filed Jan. 31, 2013, the content of each of the aforementioned applications is herein incorporated by reference in their entirety.

GOVERNMENT SUPPORT

This invention was made with government support under NIH/NIBIB R44 EB008612 awarded by the National Institute of Health. The government has certain rights in the invention.

FIELD OF THE INVENTION

The present invention relates generally to clinical x-ray computed tomography. More particularly the present invention relates to a method to compensate for spectral response effects (SREs) in a photon counting detector (PCD).

BACKGROUND OF THE INVENTION

SREs distort spectrum recorded by a PCD and is nearly impossible to correct. Photon counting x-ray detectors (PCXDs) have the potential to significantly improve x-ray computed tomography (CT) by reducing dose, providing quantitative material decomposition, and enabling K-edge imaging using high-Z contrast agents such as Gd, Au or Bi. A major problem, however, is the spectral response (SR) or the distortion of the spectrum due to the following physical effects: a finite energy-resolution, Compton scattering, charge-sharing, and K escape. These effects are independent of the incident count rate; thus, the transmitted spectrum is always distorted. If uncompensated, they result in image artifacts and inaccurate material decomposition.

In current research, a computational model of the SR, or a spectral response function (SRF), was developed based on measurements with a synchrotron. The SRF was then integrated into a forward imaging process and a maximum likelihood method was proposed to estimate line integrals of the x-ray attenuation coefficients of basis functions. The Nelder-Mead method, used as an optimization method in this research, requires numerous function evaluations and is often slower to converge than gradient-based methods. Even though the Nelder-Mead method usually converges to the minimum of the cost function, there are not many theorems from optimization theory to guarantee convergence in general cases.

It would therefore be advantageous to provide a system for correcting for the SREs recorded by PCDs.

SUMMARY OF THE INVENTION

The foregoing needs are met, to a great extent, by the present invention, wherein in one aspect system for imaging an object includes an x-ray generator configured to produce photons and a computing device. More particularly, the computing device is configured to model the photons in multiple energy bins. The computing device is also configured to attenuate the photons using a material decomposition approach, such that the photons are then incident on a PCXD pixel, where an x-ray spectrum is distorted as described by an SR of the PCXD. Additionally, the computing device is configured to determine the output of one of the multiple energy bins by finding counts within a corresponding energy range of the x-ray spectrum that has been distorted.

In accordance with an aspect of the present invention, the system further includes an increment between energy bins being 1 keV. The computing device is further configured to model an energy dependent x-ray attenuation coefficient $f(\underline{x}, E)$ by a sum of L basis materials, where $\underline{x}$ is a location and E is an energy using the algorithm, $$f(\underline{x},E) = \sum_{k=1}^{L} a_k(\underline{x})\rho_k \mu_k^{(p)}(E),$$

where $\rho_k$ is a density, $\mu_k^{(p)}(E)$ is a mass attenuation coefficient, and $a_k(\underline{x})$ is a coefficient of a $k^{th}$ basis material. Additionally, the SR is measured for at least one input energy ($E_0$), using a radioisotope at a low count rate to obtain a recorded spectrum. The recorded spectrum is normalized by an area-under-the-curve to obtain a value for SRF.

In accordance with yet another aspect of the present invention, the SRF is an impulse response of the PCXD to an energy impulse at $E_0$ and normalized to 1. The SRF is determined using the algorithm $$D_{SRF}(E; E_0) = w D_G(E; E_0) + (1-w) D_T(E; E_0),$$

$$D_G(E; E_0) = \frac{1}{\sqrt{2\pi}\,\sigma(E_0)} \exp\left(-\frac{(E-E_0)^2}{2\sigma^2(E_0)}\right),$$

$$\sigma(E_0) = k\sqrt{E_0} \quad (E_0 \text{ in keV}),$$

$$D_T(E; E_0) = \begin{cases} 1/(E_0 - E_{min}), & E_{min} \le E \le E_0, \\ 0, & \text{otherwise} \end{cases}.$$

In accordance with another aspect of the present invention, a method for imaging an object includes configuring an x-ray generator to produce photons, directing the photons to the object to be imaged, and gathering data from the photons contacting the object to be imaged. The method includes transmitting the data to a non-transitory computer readable medium programmed to model the photons in multiple energy bins and attenuate the photons using a material decomposition approach, such that the photons are then incident on a PCXD pixel, where an x-ray spectrum is distorted as described by an SR of the PCXD. Additionally, the non-transitory computer readable medium is configured to determine the output of one of the multiple energy bins by finding counts within a corresponding energy range of the x-ray spectrum that has been distorted.

In accordance with another aspect of the present invention, the method includes setting an increment between energy bins to be 1 keV. The method also includes modeling an energy dependent x-ray attenuation coefficient $f(\underline{x}, E)$ by a sum of L basis materials, where $\underline{x}$ is a location and E is an energy using the algorithm, $$f(\underline{x},E) = \sum_{k=1}^{L} a_k(\underline{x})\rho_k \mu_k^{(p)}(E),$$

where $\rho_k$ is a density, $\mu_k^{(p)}(E)$ is a mass attenuation coefficient, and $a_k(\underline{x})$ is a coefficient of a $k^{th}$ basis material.

In accordance with yet another aspect of the present invention, the method includes measuring the SR for at least one input energy ($E_0$), using a radioisotope at a low count rate to obtain a recorded spectrum and normalizing the recorded spectrum by an area-under-the-curve to obtain a value for SRF. Also, the method includes defining the SRF as an impulse response of the PCXD to an energy impulse at $E_0$ and normalized to 1. The SRF is determined using the algorithm $$D_{SRF}(E; E_0) = wD_G(E; E_0) + (1 - w)D_T(E; E_0),$$

$$D_G(E; E_0) = \frac{1}{\sqrt{2\pi}\,\sigma(E_0)} \exp\left(-\frac{(E - E_0)^2}{2\sigma^2(E_0)}\right),$$

$$\sigma(E_0) = k\sqrt{E_0} \quad (E_0 \text{ in keV}),$$

$$D_T(E; E_0) = \begin{cases} 1/(E_0 - E_{min}), & E_{min} \le E \le E_0, \\ 0, & \text{otherwise} \end{cases}.$$

In accordance with still another aspect of the present invention, the method includes performing a calibration process before imaging. Additionally, the method includes obtaining x-ray tube spectrum and SRF during the calibration process and reconstructing images from projection data collected from the photons. The method also includes using the SRF to reconstruct the image, creating a quantitative k-edge image from the SRF reconstructed image, and reconstructing unbiased x-ray attenuation coefficient images.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 2 illustrates a diagram of pseudo code of the optimization method, according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The x-ray spectrum recorded by a photon-counting x-ray detector (PCXD) is distorted due to the following physical effects which are independent of the count rate: finite energy-resolution, Compton scattering, charge-sharing, and Kescape. If left uncompensated, the spectral response (SR) of a PCXD due to the above effects will result in image artifacts and inaccurate material decomposition. An embodiment in accordance with the present invention provides a new SR compensation (SRC) method, using a more efficient conjugate gradient method. In this method, the first and second derivatives are directly calculated analytically. The proposed SRC uses a sinogram restoration approach, integrates the SRF as a part of a forward imaging model, and compensates for the effect of the SR by maximizing the Poisson log-likelihood of measurements. The algorithm can be evaluated using as a simulated fan-beam x-ray CT scanner.

The present invention uses an efficient conjugate gradient method in which the first and second derivatives of the cost functions are directly calculated analytically, whereas a slower optimization method that requires numerous function evaluations was used in other work. The algorithm of the present invention guarantees convergence by combining the non-linear conjugate gradient method with line searches that satisfy Wolfe conditions. Additionally, the algorithm in other work is not backed by theorems from optimization theory to guarantee convergence. Quantitative K-edge imaging is possible only when SR compensation is done.

Figure 1B:
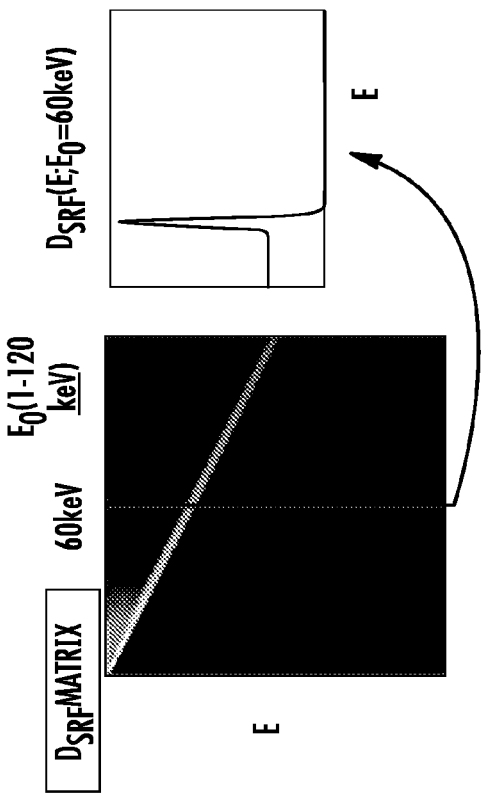
FIG. 1B illustrates a photographic and graphical view of a spectral response function according to an embodiment of the present invention.
Figure 1A:
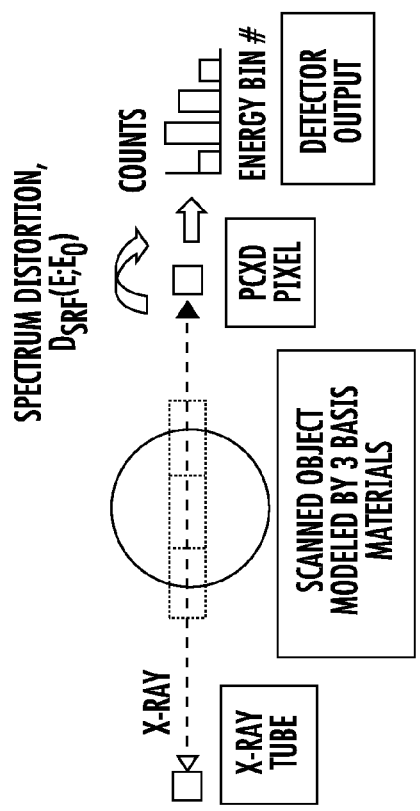
FIG. 1A illustrates a schematic diagram of a forward imaging process according to an embodiment of the present invention.

The proposed method uses the forward imaging process shown in FIG. 1A, which accurately models the imaging system and the scanned object. A polychromatic x-ray spectrum exiting from a bowtie filter is modeled by the number of photons in multiple energy bins with a 1 keV increment. The photons are then attenuated by the object following Beer's law, which is modeled using a material decomposition approach, described further, herein. The x-ray photons are then incident on a PCXD pixel, where the x-ray spectrum is distorted as described by the SR of the PCXD, also described further herein. The output of an energy bin is counts within the corresponding energy range of the distorted spectrum. The x-ray tube spectrum and SRF can be obtained during calibration processes. The object being imaged is a spatial distribution of the energy-dependent x-ray attenuation coefficient: f(x, E), where x is a location and E is an energy. Using the concept of material decomposition, f(x, E) can be modeled accurately by a sum of L basis materials, $$f(\underline{x}, E) = \Sigma_{k=1}^{L} a_k(\underline{x}) \rho_k \mu_k^{(p)}(E), \qquad (1)$$

where $\rho_k$ is the density, $\mu_k^{(p)}(E)$ is the mass attenuation coefficient, and $a_k(x)$ is the coefficient of the kth basis material (thus, the fraction-by-weight of basis material k at location $\underline{x}$ is $a_k(\underline{x})\rho_k/\Sigma_{k=1}^L a_k(\underline{x})\rho k\mu_k^{(\rho)}(E)$. Note that two basis materials (e.g., bone and water) can be replaced by two physical interactions between x-ray photons and materials, i.e., the photoelectric effect and Compton scattering.

The SR for monochromatic incident x-ray is measured for a few input energies, $E_0$'s, using radioisotopes at a very low count rate (to avoid count rate dependent physical effects such as pulse pileup effects). The recorded spectrum is normalized by the area-under-the-curve to obtain the SRF. Thus, the SRF is the impulse response of the PCXD to an energy impulse at $E_0$, normalized to 1. SRFs vary gradually depending on the input energy $E_0$.

The mathematical equation for the SRF, $D_{SRF}(E; E_0)$, is defined to model the above measurements with a few parameters. The SR for $E_0$ is a weighted summation of two normalized functions for a photopeak $(D_G)$ and a long tail $(D_T)$. The photopeak is modeled by a Gaussian bell curve with a parameter $\sigma(E_0)$ centered at $E_0$. The tail is a constant that extends from $E_0$ down to $E_{min}$. The SRF can then be described as $$D_{SRF}(E; E_0) = wD_G(E; E_0) + (1 - w)D_T(E; E_0),$$

$$D_G(E; E_0) = \frac{1}{\sqrt{2\pi}\,\sigma(E_0)} \exp\left(-\frac{(E - E_0)^2}{2\sigma^2(E_0)}\right),$$

$$\sigma(E_0) = k\sqrt{E_0} \quad (E_0 \text{ in keV}),$$

$$D_T(E; E_0) = \begin{cases} 1/(E_0 - E_{min}), & E_{min} \leq E \leq E_0, \\ 0, & \text{otherwise} \end{cases}.$$

There are three parameters that change the SRF: k for the width of the photopeak; w for a balance between the photopeak and the tail; and $E_{min}$ for the minimum tail energy or noise floor ($E_{min}$ is fixed).

A method to reconstruct images from the projection data, is now described. A cost function computed for each ray i, $\Phi(\underline{l})$, is a negative Poisson log-likelihood of recorded photon counts in energy bins. Independent variables of the cost function are the line integral of the coefficient of each basis material, $ak(x)$: $l_{i,k}=\int_{ray(i)} a_k(x)d\underline{x}$. For each ray, the conjugate gradient method estimates line integrals $l_{i,k}$ by minimizing the cost function. Basis material images, $a_k(\underline{x})$, are then reconstructed from the estimated $l_{i,k}$ using filtered back projection. A monoenergetic CT image at a desirable energy $E_r$, $f(\underline{x},E_r)$, can then be synthesized from $a_k(\underline{x})$ using Eq. 1.

For the cost function used to estimate $l_{i,k}$, $N_{b,e}$ is the mean number of photon counts exiting the x-ray tube with energy e, which can be denoted as a vector $\underline{N}_b$ [$N_{b,1}, \ldots, N_{b,e}, \ldots N_{b,Emax}$] where e is an index variable that takes discrete values over energy, from 1 to $E_{max}=120$ keV with 1 keV increment and [ ]' is the transpose of [ ]. Using Eq. 1, the spectrum incident on the detector along ray i after attenuation by the object is expressed as $$N_{d,e}(\underline{l}) = N_{b,e} \exp(\Sigma_{k=1}^L \rho_k \mu_k^{(\rho)}, e^1 k) \text{ and } \underline{l}[l_1 \ldots l_L]'$$

Here i is dropped from $l_{i,k}$ for better readability. The distorted spectrum due to SR can then be calculated as $\underline{N}_r(\underline{l}) = D_{SRF} * \underline{N}_d(\underline{l})$, where * denotes a matrix multiplication, and the matrix $D_{SRF}$ is the discretized $D_{SRF}(E;E_0)$ over energy, as illustrated in FIG. 1B. The mean counts in the nth energy bin of the detector output is then the sum of counts in the distorted spectrum over the energy window, $$\bar{y}_n = (l) = \sum_{e=E_{low,n}}^{E_{high,n}} \underline{N}_{r,e}(l).$$

Multinomial selection of Poisson variables yields Poisson variables; thus, the recorded counts are Poisson distributed.

Thus, the negative Poisson log-likelihood for ray i is $$\Phi(\underline{l}) = -L(\underline{y}:\underline{\bar{y}}(\underline{l})) = \sum_{n=1}^{N_{bin}} \bar{y}_n(l) - y_n \log \bar{y}_n(l),$$

where $N_{bin}$ is the number of energy bins, and $\underline{y}[y_1 \ldots y_{Nbin}]'$ is the raw data.

The optimization method is described in this section and illustrated in FIG. 2. The direction of the line search is computed using the conjugate gradient method. Each line search is performed using a quasi-Newton method. The gradient ($\nabla\Phi$) and Hessian ($\nabla2\Phi$, not shown here) used by the conjugate gradient and quasi-Newton methods, respectively, are computed analytically using the chain rule:

$$\nabla\Phi = \left[\frac{\partial\Phi(\underline{l})}{\partial l_1} \ldots \frac{\partial\Phi(\underline{l})}{\partial l_L}\right]',$$

$$\frac{\partial\Phi(\underline{l})}{\partial l_k} = \sum_n^{N_{bin}} (1 - y_n/\bar{y}_n(\underline{l}))\frac{\partial\bar{y}_n(\underline{l})}{\partial l_k},$$

$$\frac{\partial\bar{y}_n(\underline{l})}{\partial l_k} = \sum_{e=E_{low,n}}^{E_{high,n}} \frac{\partial\underline{N}_{r,e}(\underline{l})}{\partial l_k},$$

$$\frac{\partial\underline{N}_{r,e}(\underline{l})}{\partial l_k} = \sum_{e'=1}^{E_{max}} D_{SRF}(e, e')\frac{\partial\underline{N}_{d,e'}(\underline{l})}{\partial l_k},$$

and $$\frac{\partial N_{d,e}(\underline{l})}{\partial l_k} = N_{b,e} \exp\left(-\sum_{k'=1}^L \rho_{k'}\mu_{k',ek'}^{(\rho)l_i}\right)(-\rho_k\mu_{k,e}^{(\rho)}).$$

The algorithm and method of the present invention discussed herein can be evaluated using computer simulations. A first evaluation is carried out using a single detector pixel with noise free data for a simple sanity check. Three basis materials with various thicknesses are placed between the detector and the x-ray tube; and the PCXD output is measured under scan conditions similar to those outlined below. The bias of the estimated thicknesses was within 0.2% of the true thicknesses. A second evaluation is performed using a fan-beam x-ray CT scanner geometry, as outlined below.

Figure 3:
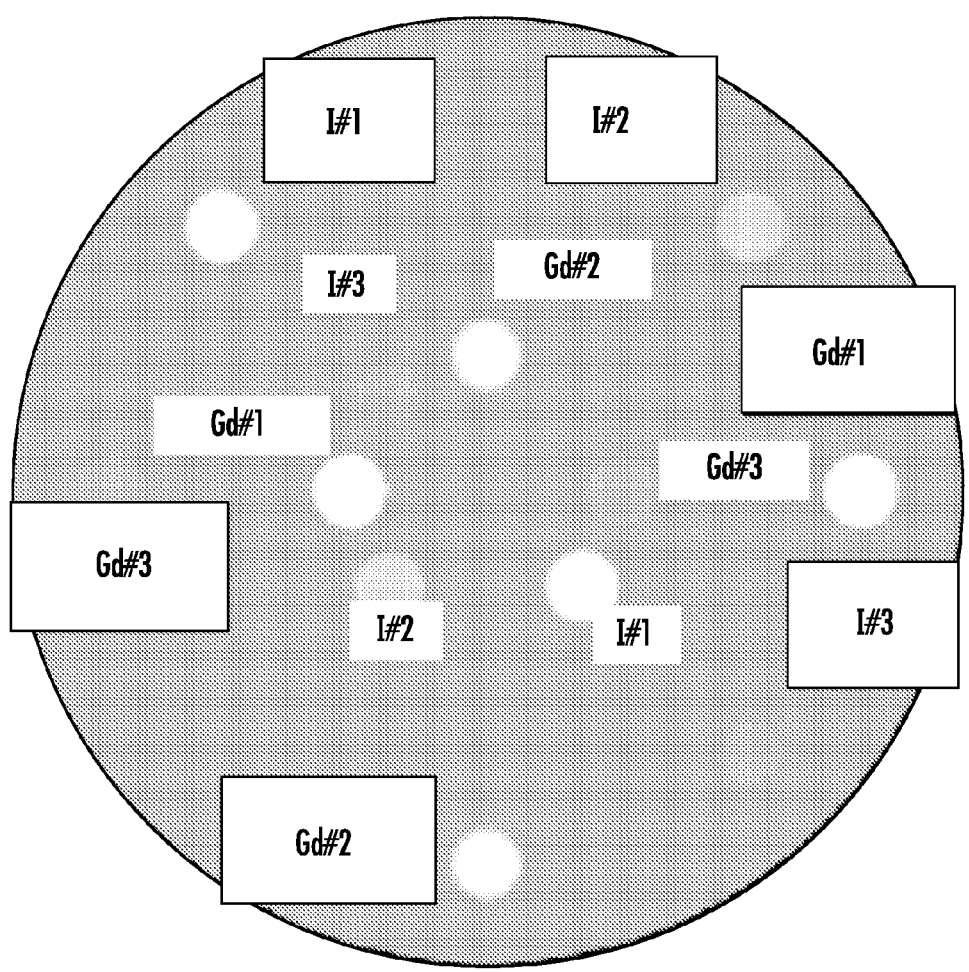
FIG. 3 illustrates a view of a phantom, according to an embodiment of the present invention.

In the first and second evaluations, X-rays are produced at 120 kVp with a 5 mm Al flat filter and a count rate at the detector of $2.1 \times 10^6$ photons/sec/mm²/mA. The source-to-isocenter distance is 570 mm and the source-to-detector distance is 1040 mm. The phantom is a water cylinder with a diameter of 28 cm containing 12 inserts with a diameter of 2 cm each, as illustrated in FIG. 3. These inserts contain elemental solutions of I or Gd in water with concentrations of 0.2 (labeled as #1 in FIG. 3), 0.02 (#2) or 0.002 (#3) mol/L. The arc detector has 768 of 1 mm×1 mm detector pixels. Photon counts from 10 pixels are combined in the z-direction, and so the reconstructed slice thickness at the iso-center would be 5.5 mm. The PCXD has 6 energy bins at thresholds of 30, 40, 50, 65, 80, and 100 keV. The SRF parameters are k=0.4 and w=0.33. The scan is performed with 216 mAs and 1000 views are acquired over 360°.

Images taken using the algorithm and method of the present invention described herein can be reconstructed by two reconstruction methods, one with SRF compensation with the proposed algorithm, and the other without compensation using an identity matrix for DSRF. Water ($\rho$=1 g/cc), I ($\rho$=0.038 g/cc), and Gd (p=0.04 g/cc) can be used as basis materials. The basis material images (ak($\underline{x}$), k=1, 2, 3) are reconstructed followed by a monoenergetic CT image at 75 keV, f(x, Er=75 keV). An energy of 75 keV was chosen to minimize the noise at the center of the image. The bias in x-ray attenuation coefficient image reconstructed using the proposed SRC algorithm is zero, as illustrated in FIGS. 5-7.

Figure 4:
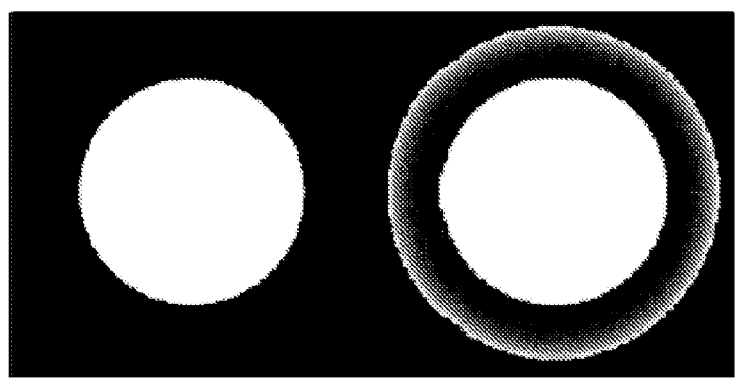
FIG. 4 illustrates views of basis images with and without SR compensation, according to an embodiment of the present invention. Images with SR compensation are on the left and images with SR compensation are on the right.
Figure 4:
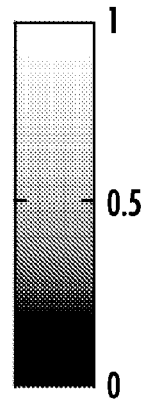
Figure 4:
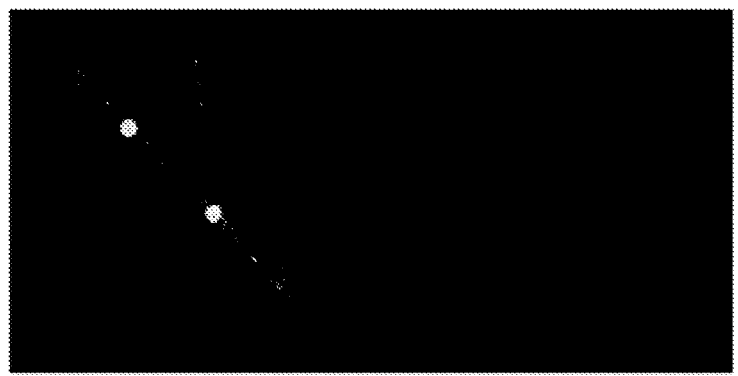
Figure 4:
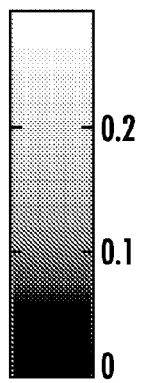
Figure 4:
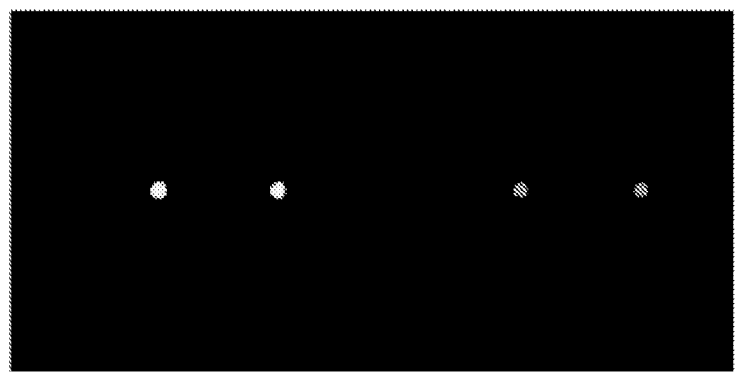
Figure 4:
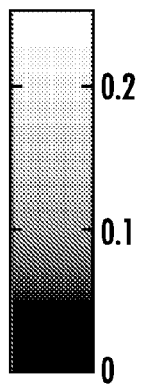
Figure 5:
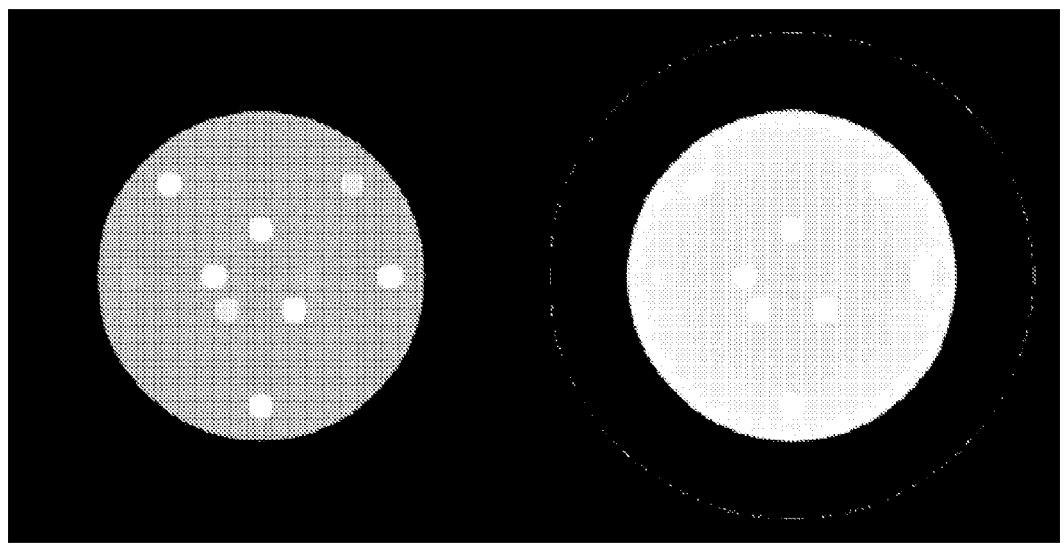
FIG. 5 illustrates a view of CT images with and without SR compensation, according to an embodiment of the present invention. Images with SR compensation are on the left and images with SR compensation are on the right.
Figure 6:
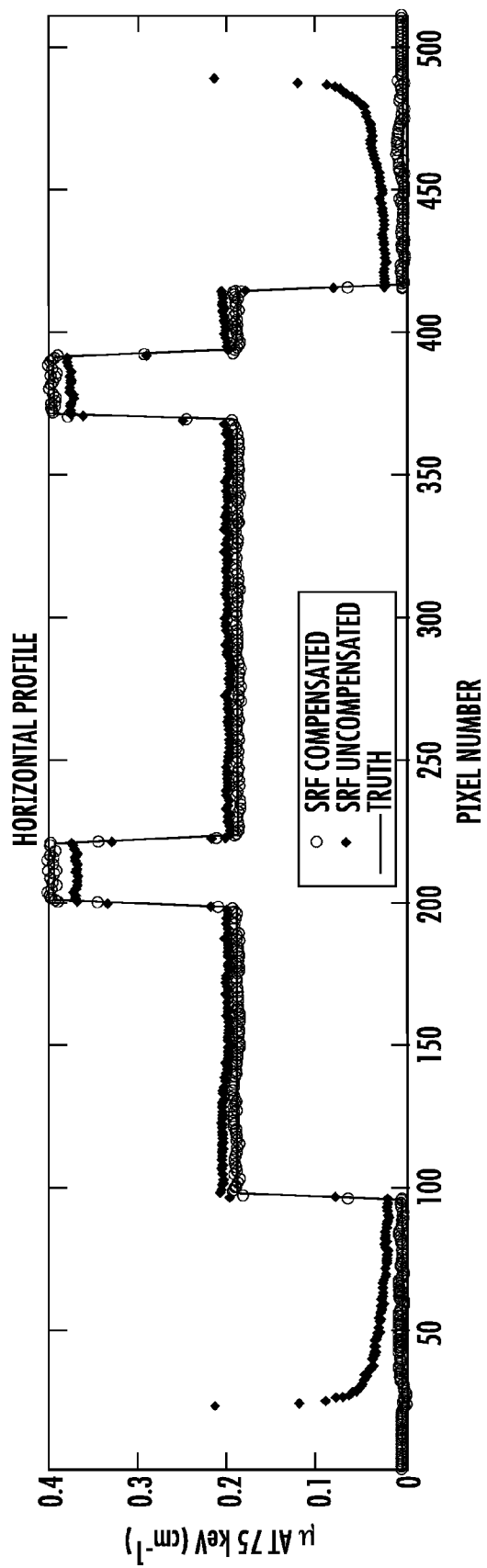
FIG. 6 illustrates a graphical view of the images shown in FIG. 5, according to an embodiment of the present invention.
Figure 7:
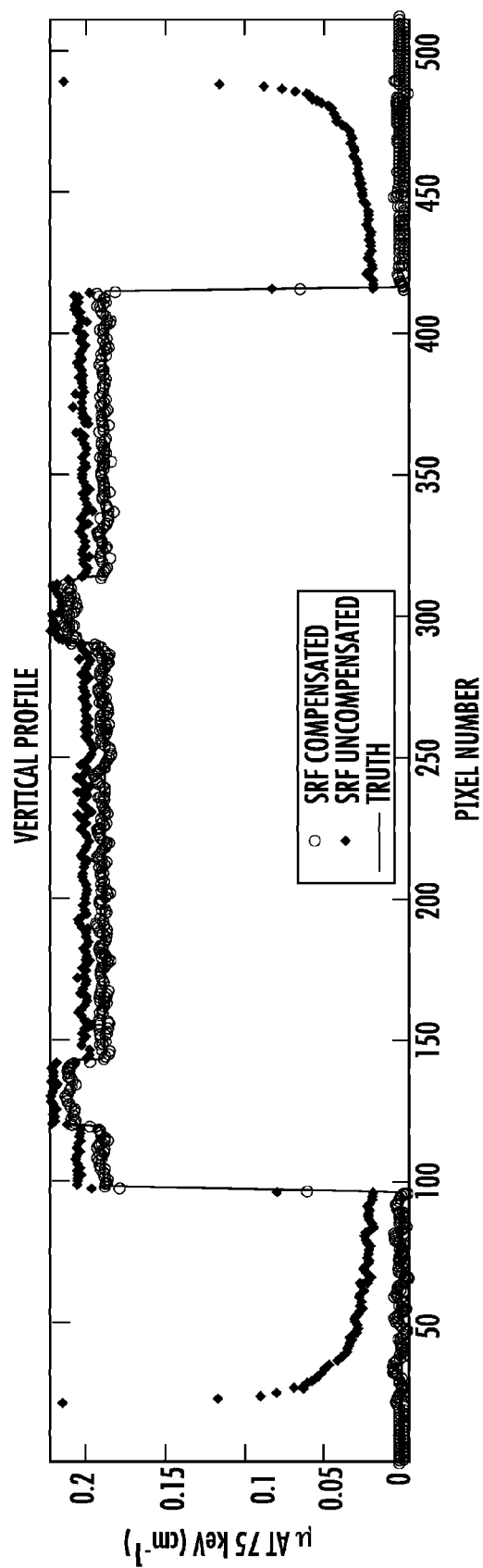
FIG. 7 illustrates a graphical view of images shown in FIG. 5, according to an embodiment of the present invention.

Without the SR compensation provided by the present invention, images exhibit cupping, streak, and ring artifacts, as illustrated in FIGS. 5-7. The bias can be as much as 11%, as illustrated in FIG. 7. Thus, it is concluded that unbiased x-ray attenuation coefficient images can be reconstructed with the proposed algorithm. Material decomposition is only possible and accurate with SRC, as illustrated in FIG. 4. Thus, quantitative K-edge imaging is possible only with the proposed algorithm and the method of the present invention or variations thereof known to or conceivable by one of skill in the art.

It should also be noted that the method of the present invention described above, as well as the algorithms associated with the methods of the present invention and also described above, can be executed using a computing device. The computing device can be loaded with a non-transitory computer readable medium (CRM) programmed to execute the method and algorithms of the present invention. The CRM can take any suitable form known to or conceivable to one of skill in the art. A CRM is understood to be any article of manufacture readable by a computer. Such CRM includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art. The computing device can be incorporated directly into the imaging device or can be networked with the imaging device in a manner known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for imaging an object comprising:
an x-ray generator configured to produce photons;
a non-transitory computer readable medium programmed to:
model the photons in multiple energy bins;
attenuate the photons using a material decomposition approach, such that the photons are then incident on a PCXD pixel, where an x-ray spectrum is distorted as described by an SR of the PCXD;
determine the output of one of the multiple energy bins by finding counts within a corresponding energy range of the x-ray spectrum that has been distorted.

2. The system of claim 1 further comprising an increment between energy bins being 1 keV.

3. The system of claim 1 wherein the non-transitory computer readable medium is further programmed to model an energy dependent x-ray attenuation coefficient f($\underline{x}$, E) by a sum of L basis materials, where $\underline{x}$ is a location and E is an energy using the algorithm, $$f(\underline{x},E)=\Sigma_{k=1}^{L}a_k(\underline{x})\rho_k\mu_k^{(\rho)}(E),$$

where $\rho_k$ is a density, $\mu_k^{(\rho)}(E)$ is a mass attenuation coefficient, and $a_k(\underline{x})$ is a coefficient of a $k^{th}$ basis material.

4. The system of claim 1 wherein the SR is measured for at least one input energy ($E_0$), using a radioisotope at a low count rate to obtain a recorded spectrum.

5. The system of claim 4 wherein the recorded spectrum is normalized by an area-under-the-curve to obtain a value for SRF.

6. The system of claim 5 wherein the SRF is an impulse response of the PCXD to an energy impulse at $E_0$ and normalized to 1.

7. The system of claim 5 wherein the SRF is determined using the algorithm $$D_{SRF}(E; E_0) = wD_G(E; E_0) + (1 - w)D_T(E; E_0),$$

$$D_G(E; E_0) = \frac{1}{\sqrt{2\pi}\,\sigma(E_0)} \exp\left(-\frac{(E - E_0)^2}{2\sigma^2(E_0)}\right),$$

$$\sigma(E_0) = k\sqrt{E_0} \quad (E_0 \text{ in keV}),$$

$$D_T(E; E_0) = \begin{cases} 1/(E_0 - E_{min}), & E_{min} \le E \le E_0, \\ 0, & \text{otherwise} \end{cases}.$$

8. A method for imaging an object comprising:
configuring an x-ray generator to produce photons;
directing the photons to the object to be imaged;
gathering data from the photons contacting the object to be imaged;
transmitting the data to a non-transitory computer readable medium programmed to:
model the photons in multiple energy bins;
attenuate the photons using a material decomposition approach, such that the photons are then incident on a PCXD pixel, where an x-ray spectrum is distorted as described by an SR of the PCXD;
determine the output of one of the multiple energy bins by finding counts within a corresponding energy range of the x-ray spectrum that has been distorted.

9. The method of claim 8 further comprising setting an increment between energy bins to be 1 keV.

10. The method of claim 8 further comprising modeling an energy dependent x-ray attenuation coefficient f($\underline{x}$, E) by a sum of L basis materials, where $\underline{x}$ is a location and E is an energy using the algorithm, $$f(\underline{x},E)=\Sigma_{k=1}^{L} a_k(\underline{x})\rho_k\mu_k^{(\rho)}(E),$$

where $\rho_k$ is a density, $\mu_k^{(\rho)}(E)$ is a mass attenuation coefficient, and $a_k(\underline{x})$ is a coefficient of a $k^{th}$ basis material.

11. The method of claim 8 further comprising measuring the SR for at least one input energy ($E_0$), using a radioisotope at a low count rate to obtain a recorded spectrum.

12. The method of claim 11 further comprising normalizing the recorded spectrum by an area-under-the-curve to obtain a value for SRF.

13. The method of claim 12 further comprising defining the SRF as an impulse response of the PCXD to an energy impulse at $E_0$ and normalized to 1.

14. The method of claim 12 further comprising determining SRF using the algorithm $$D_{SRF}(E; E_0) = wD_G(E; E_0) + (1-w)D_T(E; E_0),$$

$$D_G(E; E_0) = \frac{1}{\sqrt{2\pi}\,\sigma(E_0)} \exp\left(-\frac{(E-E_0)^2}{2\sigma^2(E_0)}\right),$$

$$\sigma(E_0) = k\sqrt{E_0} \quad (E_0 \text{ in keV}),$$

$$D_T(E; E_0) = \begin{cases} 1/(E_0 - E_{min}), & E_{min} \leq E \leq E_0, \\ 0, & \text{otherwise} \end{cases}.$$

15. The method of claim 8 further comprising performing a calibration process before imaging.

16. The method of claim 8 further comprising obtaining x-ray tube spectrum and SRF during the calibration process.

17. The method of claim 8 further comprising reconstructing images from projection data collected from the photons.

18. The method of claim 14 further comprising using the SRF to reconstruct the image.

19. The method of claim 18 further comprising creating a quantitative k-edge image from the SRF reconstructed image.

20. The method of claim 19 further comprising reconstructing unbiased x-ray attenuation coefficient images.

* * * * *